US012636063B2

(12) United States Patent
Dunning

(10) Patent No.: US 12,636,063 B2
(45) Date of Patent: May 26, 2026

(54) MOTION SENSING ELECTROSURGICAL DEVICES

(71) Applicant: Covidien LP, Mansfield, MA (US)

(72) Inventor: James E. Dunning, Boulder, CO (US)

(73) Assignee: Covidien LP, Mansfield, MA (US)

( * ) Notice: Subject to any disclaimer, the term of this patent is extended or adjusted under 35 U.S.C. 154(b) by 882 days.

(21) Appl. No.: 17/742,580

(22) Filed: May 12, 2022

(65) Prior Publication Data

US 2022/0395311 A1 Dec. 15, 2022

Related U.S. Application Data

(60) Provisional application No. 63/209,090, filed on Jun. 10, 2021.

(51) Int. Cl.
A61B 18/12 (2006.01)
A61B 18/14 (2006.01)
A61B 18/00 (2006.01)

(52) U.S. Cl.
CPC ...... A61B 18/1206 (2013.01); A61B 18/1445 (2013.01); *A61B 2018/00589* (2013.01); *A61B 2018/00601* (2013.01); *A61B 2018/00702* (2013.01); *A61B 2018/00875* (2013.01); *A61B 2018/126* (2013.01); *A61B 2018/1462* (2013.01)

(58) Field of Classification Search
CPC ............ A61B 18/1206; A61B 18/1445; A61B 2018/00589; A61B 2018/00601; A61B 2018/00636; A61B 2018/00773; A61B 2018/126
See application file for complete search history.

(56) References Cited

U.S. PATENT DOCUMENTS

| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,693,106 | A | 11/1954 | Henry |
| 2,827,056 | A | 3/1958 | Degelman |
| 2,849,611 | A | 8/1958 | Adams |

(Continued)

FOREIGN PATENT DOCUMENTS

| DE | 179607 C | 11/1906 |
| DE | 390937 C | 3/1924 |

(Continued)

OTHER PUBLICATIONS

US 6,878,148 B2, 04/2005, Goble et al. (withdrawn)

(Continued)

*Primary Examiner* — Michael F Peffley
*Assistant Examiner* — Samantha M Good
(74) *Attorney, Agent, or Firm* — Carter, DeLuca & Farrell, LLP

(57) ABSTRACT

An electrosurgical system may include an electrosurgical generator configured to generate electrosurgical energy; and an electrosurgical instrument coupled to the electrosurgical generator. The electrosurgical instrument may include a motion and/or position sensor, where the electrosurgical generator is configured to control the electrosurgical energy based on a sensor signal from the sensor.

13 Claims, 6 Drawing Sheets

(56) References Cited

U.S. PATENT DOCUMENTS

| | | | |
|---|---|---|---|
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |

(56)  References Cited

U.S. PATENT DOCUMENTS

| | | | |
|---|---|---|---|
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,057,105 A | 10/1991 | Malone et al. |
| 5,067,953 A | 11/1991 | Feucht |
| 5,075,839 A | 12/1991 | Fisher et al. |
| 5,078,153 A | 1/1992 | Nordlander et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,113,116 A | 5/1992 | Wilson |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,216,338 A | 6/1993 | Wilson |
| 5,230,623 A | 7/1993 | Guthrie et al. |
| 5,233,515 A | 8/1993 | Cosman |
| 5,234,427 A | 8/1993 | Ohtomo et al. |
| 5,244,462 A | 9/1993 | Delahuerga et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,269,780 A | 12/1993 | Roos |
| 5,271,413 A | 12/1993 | Dalamagas et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,396,194 A | 3/1995 | Williamson et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen et al. |
| 5,445,638 A | 8/1995 | Rydell et al. |
| 5,448,466 A | 9/1995 | Erckert |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,498,261 A | 3/1996 | Strul |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |

(56)                  References Cited

U.S. PATENT DOCUMENTS

| | | | |
|---|---|---|---|
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Adtkow et al. |
| 5,542,916 A | 8/1996 | Hirsch et al. |
| 5,545,161 A | 8/1996 | Mran |
| 5,554,172 A | 9/1996 | Horner et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Chi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,693,082 A | 12/1997 | Warner et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,835 A | 8/1999 | Mackey |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,002,968 A | 12/1999 | Edwards |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |

(56)  References Cited

U.S. PATENT DOCUMENTS

| | | | |
|---|---|---|---|
| 6,055,458 | A | 4/2000 | Cochran et al. |
| 6,056,745 | A | 5/2000 | Panescu et al. |
| 6,056,746 | A | 5/2000 | Goble et al. |
| 6,059,780 | A | 5/2000 | Gough et al. |
| 6,059,781 | A | 5/2000 | Yamanashi et al. |
| 6,063,075 | A | 5/2000 | Mihori |
| 6,063,078 | A | 5/2000 | Wittkampf |
| 6,066,137 | A | 5/2000 | Greep |
| 6,068,627 | A | 5/2000 | Orszulak et al. |
| 6,074,089 | A | 6/2000 | Hollander et al. |
| 6,074,386 | A | 6/2000 | Goble et al. |
| 6,074,388 | A | 6/2000 | Tockweiler et al. |
| 6,080,149 | A | 6/2000 | Huang et al. |
| 6,088,614 | A | 7/2000 | Swanson |
| 6,089,864 | A | 7/2000 | Buckner et al. |
| 6,090,123 | A | 7/2000 | Culp et al. |
| 6,093,186 | A | 7/2000 | Goble |
| 6,102,497 | A | 8/2000 | Ehr et al. |
| 6,102,907 | A | 8/2000 | Smethers et al. |
| 6,104,248 | A | 8/2000 | Carver |
| 6,106,524 | A | 8/2000 | Eggers et al. |
| 6,113,591 | A | 9/2000 | Whayne et al. |
| 6,113,592 | A | 9/2000 | Taylor |
| 6,113,593 | A | 9/2000 | Tu et al. |
| 6,113,596 | A | 9/2000 | Hooven et al. |
| 6,123,701 | A | 9/2000 | Nezhat |
| 6,123,702 | A | 9/2000 | Swanson et al. |
| 6,132,429 | A | 10/2000 | Baker |
| 6,139,349 | A | 10/2000 | Wright |
| 6,142,992 | A | 11/2000 | Cheng et al. |
| 6,144,937 | A | 11/2000 | Ali |
| 6,155,975 | A | 12/2000 | Urich et al. |
| 6,162,184 | A | 12/2000 | Swanson et al. |
| 6,162,217 | A | 12/2000 | Kannenberg et al. |
| 6,165,169 | A | 12/2000 | Panescu et al. |
| 6,165,173 | A | 12/2000 | Kamdar et al. |
| 6,171,304 | B1 | 1/2001 | Netherly |
| 6,173,713 | B1 | 1/2001 | Dawson |
| 6,183,468 | B1 | 2/2001 | Swanson et al. |
| 6,186,147 | B1 | 2/2001 | Cobb |
| 6,188,211 | B1 | 2/2001 | Rincon-Mora et al. |
| 6,193,713 | B1 | 2/2001 | Geistert et al. |
| 6,197,023 | B1 | 3/2001 | Muntermann |
| 6,200,314 | B1 | 3/2001 | Sherman |
| 6,203,541 | B1 | 3/2001 | Keppel |
| 6,210,403 | B1 | 4/2001 | Klicek |
| 6,216,704 | B1 | 4/2001 | Ingle et al. |
| 6,222,356 | B1 | 4/2001 | Taghizadeh-Kaschani |
| 6,228,078 | B1 | 5/2001 | Eggers et al. |
| 6,228,080 | B1 | 5/2001 | Gines |
| 6,228,081 | B1 | 5/2001 | Goble |
| 6,231,569 | B1 | 5/2001 | Bek et al. |
| 6,232,556 | B1 | 5/2001 | Daugherty et al. |
| 6,235,020 | B1 | 5/2001 | Cheng et al. |
| 6,235,022 | B1 | 5/2001 | Hallock et al. |
| 6,237,604 | B1 | 5/2001 | Burnside et al. |
| 6,238,387 | B1 | 5/2001 | Miller, III |
| 6,238,388 | B1 | 5/2001 | Ellman et al. |
| 6,241,723 | B1 | 6/2001 | Heim et al. |
| 6,241,725 | B1 | 6/2001 | Cosman |
| 6,243,654 | B1 | 6/2001 | Johnson et al. |
| 6,245,061 | B1 | 6/2001 | Panescu et al. |
| 6,245,063 | B1 | 6/2001 | Uphoff |
| 6,245,065 | B1 | 6/2001 | Panescu et al. |
| 6,246,912 | B1 | 6/2001 | Sluijter et al. |
| 6,251,106 | B1 | 6/2001 | Becker et al. |
| 6,254,422 | B1 | 7/2001 | Feye-Hohmann |
| 6,258,085 | B1 | 7/2001 | Eggleston |
| 6,259,937 | B1 | 7/2001 | Schulman et al. |
| 6,261,285 | B1 | 7/2001 | Novak et al. |
| 6,261,286 | B1 | 7/2001 | Goble et al. |
| 6,267,760 | B1 | 7/2001 | Swanson |
| 6,270,497 | B1 | 8/2001 | Sekino et al. |
| 6,273,886 | B1 | 8/2001 | Edwards et al. |
| 6,275,786 | B1 | 8/2001 | Daners |
| 6,287,304 | B1 | 9/2001 | Eggers et al. |
| 6,293,941 | B1 | 9/2001 | Strul et al. |
| 6,293,942 | B1 | 9/2001 | Goble et al. |
| 6,293,943 | B1 | 9/2001 | Panescu et al. |
| 6,296,636 | B1 | 10/2001 | Cheng et al. |
| 6,304,138 | B1 | 10/2001 | Johnson |
| 6,306,131 | B1 | 10/2001 | Hareyama et al. |
| 6,306,134 | B1 | 10/2001 | Goble et al. |
| 6,309,386 | B1 | 10/2001 | Bek |
| 6,322,558 | B1 | 11/2001 | Taylor et al. |
| 6,325,799 | B1 | 12/2001 | Goble |
| 6,329,778 | B1 | 12/2001 | Culp et al. |
| 6,337,998 | B1 | 1/2002 | Behl et al. |
| 6,338,657 | B1 | 1/2002 | Harper et al. |
| 6,341,981 | B1 | 1/2002 | Gorman |
| 6,350,262 | B1 | 2/2002 | Ashley |
| 6,350,263 | B1 | 2/2002 | Wetzig et al. |
| 6,358,245 | B1 | 3/2002 | Edwards et al. |
| 6,364,877 | B1 | 4/2002 | Goble et al. |
| 6,370,408 | B1 | 4/2002 | Merchant et al. |
| 6,371,963 | B1 | 4/2002 | Nishtala et al. |
| 6,383,183 | B1 | 5/2002 | Sekino et al. |
| 6,387,092 | B1 | 5/2002 | Burnside et al. |
| 6,391,024 | B1 | 5/2002 | Sun et al. |
| 6,398,779 | B1 | 6/2002 | Buysse et al. |
| 6,398,781 | B1 | 6/2002 | Goble et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,722 | B1 | 6/2002 | Hoey et al. |
| 6,413,256 | B1 | 7/2002 | Truckai et al. |
| 6,416,509 | B1 | 7/2002 | Goble et al. |
| 6,422,896 | B2 | 7/2002 | Aoki et al. |
| 6,423,057 | B1 | 7/2002 | He et al. |
| 6,424,186 | B1 | 7/2002 | Quimby et al. |
| 6,426,886 | B1 | 7/2002 | Goder |
| 6,427,089 | B1 | 7/2002 | Knowlton |
| 6,428,537 | B1 | 8/2002 | Swanson et al. |
| 6,436,096 | B1 | 8/2002 | Hareyama |
| 6,440,157 | B1 | 8/2002 | Shigezawa et al. |
| 6,451,015 | B1 | 9/2002 | Rittman, III et al. |
| 6,454,594 | B2 | 9/2002 | Sawayanagi |
| 6,458,121 | B1 | 10/2002 | Rosenstock et al. |
| 6,458,122 | B1 | 10/2002 | Pozzato |
| 6,464,689 | B1 | 10/2002 | Qin et al. |
| 6,464,696 | B1 | 10/2002 | Oyama et al. |
| 6,468,270 | B1 | 10/2002 | Hovda et al. |
| 6,468,273 | B1 | 10/2002 | Leveen et al. |
| 6,469,481 | B1 | 10/2002 | Tateishi |
| 6,482,201 | B1 | 11/2002 | Olsen et al. |
| 6,485,487 | B1 | 11/2002 | Sherman |
| 6,488,678 | B2 | 12/2002 | Sherman |
| 6,494,880 | B1 | 12/2002 | Swanson et al. |
| 6,497,659 | B1 | 12/2002 | Rafert |
| 6,498,466 | B1 | 12/2002 | Edwards |
| 6,506,189 | B1 | 1/2003 | Rittman, III et al. |
| 6,508,815 | B1 | 1/2003 | Strul et al. |
| 6,511,476 | B2 | 1/2003 | Hareyama |
| 6,511,478 | B1 | 1/2003 | Burnside et al. |
| 6,514,251 | B1 | 2/2003 | Ni et al. |
| 6,517,538 | B1 | 2/2003 | Jacob et al. |
| 6,522,931 | B2 | 2/2003 | Manker et al. |
| 6,524,308 | B1 | 2/2003 | Muller et al. |
| 6,537,272 | B2 | 3/2003 | Christopherson et al. |
| 6,544,258 | B2 | 4/2003 | Fleenor et al. |
| 6,544,260 | B1 | 4/2003 | Markel et al. |
| 6,546,270 | B1 | 4/2003 | Goldin et al. |
| 6,547,786 | B1 | 4/2003 | Goble |
| 6,557,559 | B1 | 5/2003 | Eggers et al. |
| 6,558,376 | B2 | 5/2003 | Bishop |
| 6,558,377 | B2 | 5/2003 | Lee et al. |
| 6,560,470 | B1 | 5/2003 | Pologe |
| 6,562,037 | B2 | 5/2003 | Paton et al. |
| 6,565,559 | B2 | 5/2003 | Eggleston |
| 6,565,562 | B1 | 5/2003 | Shah et al. |
| 6,575,969 | B1 | 6/2003 | Rittman, III et al. |
| 6,578,579 | B2 | 6/2003 | Burnside et al. |
| 6,579,288 | B1 | 6/2003 | Swanson et al. |

(56)  References Cited

U.S. PATENT DOCUMENTS

| | | | |
|---|---|---|---|
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wårdell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano et al. |
| 6,645,198 B1 | 11/2003 | Bommannan et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,514 B2 | 11/2003 | Ellman et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim et al. |
| 6,693,782 B1 | 2/2004 | Lash |
| 6,695,837 B2 | 2/2004 | Howell |
| 6,696,844 B2 | 2/2004 | Wong et al. |
| 6,700,076 B2 | 3/2004 | Sun et al. |
| 6,712,813 B2 | 3/2004 | Ellman et al. |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano et al. |
| 6,733,495 B1 | 5/2004 | Bek et al. |
| 6,733,498 B2 | 5/2004 | Paton et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano et al. |
| 6,860,881 B2 | 3/2005 | Sturm et al. |
| 6,864,686 B2 | 3/2005 | Novak et al. |
| 6,875,210 B2 | 4/2005 | Refior et al. |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 6,997,935 B2 | 2/2006 | Anderson et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | De Ruijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |

(56) References Cited

U.S. PATENT DOCUMENTS

| | | | |
|---|---|---|---|
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,468,499 B2 | 12/2008 | Canini et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,573,693 B2 | 8/2009 | Hornung |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,736,359 B2 | 6/2010 | McPherson |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,863,984 B1 | 1/2011 | Behnke |
| 7,864,129 B2 | 1/2011 | Konishi |
| 7,879,029 B2 | 2/2011 | Jimenez |
| 7,879,033 B2 | 2/2011 | Sartor et al. |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 8,038,676 B2 | 10/2011 | Fischer |
| 8,070,746 B2 | 12/2011 | Orton et al. |
| 8,080,008 B2 | 12/2011 | Wham et al. |
| 8,083,735 B2 | 12/2011 | Morris |
| 8,096,961 B2 | 1/2012 | Orszulak et al. |
| 8,104,596 B2 | 1/2012 | Kim et al. |
| 8,105,323 B2 | 1/2012 | Buysse et al. |
| 8,113,057 B2 | 2/2012 | Orszulak et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,187,262 B2 | 5/2012 | Orszulak |
| 8,200,317 B2 | 6/2012 | Baxi et al. |
| 8,202,271 B2 | 6/2012 | Orszulak |
| 8,211,100 B2 | 7/2012 | Podhajsky et al. |
| 8,216,219 B2 | 7/2012 | Desinger et al. |
| 8,216,220 B2 | 7/2012 | Jensen et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,231,614 B2 | 7/2012 | Dunning et al. |
| 8,231,616 B2 | 7/2012 | McPherson et al. |
| 8,235,917 B2 | 8/2012 | Joseph et al. |
| 8,241,278 B2 | 8/2012 | Sartor |
| 8,242,782 B2 | 8/2012 | Brannan et al. |
| 8,248,075 B2 | 8/2012 | Brannan et al. |
| 8,257,349 B2 | 9/2012 | Orszulak |
| 8,257,350 B2 | 9/2012 | Marion |
| 8,262,652 B2 | 9/2012 | Podhajsky |
| 8,267,928 B2 | 9/2012 | Orszulak et al. |
| 8,267,929 B2 | 9/2012 | Wham et al. |
| 8,287,528 B2 | 10/2012 | Wham et al. |
| 8,287,529 B2 | 10/2012 | Orszulak |
| 8,292,883 B2 | 10/2012 | Kabaya et al. |
| 8,298,223 B2 | 10/2012 | Wham et al. |
| 8,303,337 B2 | 11/2012 | Ballard et al. |
| 8,303,580 B2 | 11/2012 | Wham et al. |
| 8,333,759 B2 | 12/2012 | Podhajsky |
| 8,346,370 B2 | 1/2013 | Haley et al. |
| 8,353,903 B2 | 1/2013 | Podhajsky |

(56)  References Cited

U.S. PATENT DOCUMENTS

| | | | |
|---|---|---|---|
| 8,353,905 B2 | 1/2013 | Jensen et al. |
| 8,377,053 B2 | 2/2013 | Orszulak |
| 8,377,054 B2 | 2/2013 | Gilbert |
| 8,382,751 B2 | 2/2013 | Gilbert et al. |
| 8,398,627 B2 | 3/2013 | Hosier |
| 8,403,924 B2 | 3/2013 | Behnke et al. |
| 8,409,186 B2 | 4/2013 | Behnke et al. |
| 8,454,590 B2 | 6/2013 | Smith |
| 8,460,284 B2 | 6/2013 | Aronow et al. |
| 8,469,956 B2 | 6/2013 | McKenna et al. |
| 8,475,447 B2 | 7/2013 | Orszulak et al. |
| 8,485,993 B2 | 7/2013 | Orszulak et al. |
| 8,486,061 B2 | 7/2013 | Podhajsky |
| 8,512,232 B2 | 8/2013 | Rothberg et al. |
| 8,523,855 B2 | 9/2013 | Keppel |
| 8,540,709 B2 | 9/2013 | Allen |
| 8,542,019 B2 | 9/2013 | Brannan et al. |
| 10,406,690 B1 | 9/2019 | Blankespoor |
| 10,573,713 B2 | 2/2020 | Wen |
| 10,761,524 B2 | 9/2020 | Wallace |
| 11,242,458 B2 | 2/2022 | Takada |
| 2002/0022836 A1 | 2/2002 | Goble et al. |
| 2002/0029036 A1 | 3/2002 | Goble et al. |
| 2003/0153908 A1 | 8/2003 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton et al. |
| 2004/0097912 A1 | 5/2004 | Gonnering |
| 2004/0133189 A1 | 7/2004 | Sakurai |
| 2004/0172016 A1 | 9/2004 | Bek et al. |
| 2004/0193021 A1 | 9/2004 | Zdeblick et al. |
| 2005/0004634 A1 | 1/2005 | Ricart et al. |
| 2005/0021020 A1 | 1/2005 | Blaha |
| 2005/0109111 A1 | 5/2005 | Manlove et al. |
| 2005/0109935 A1 | 5/2005 | Manlove et al. |
| 2005/0131390 A1 | 6/2005 | Heinrich et al. |
| 2006/0079774 A1 | 4/2006 | Anderson |
| 2006/0111711 A1 | 5/2006 | Goble |
| 2006/0155270 A1 | 7/2006 | Hancock |
| 2006/0161148 A1 | 7/2006 | Behnke |
| 2006/0191926 A1 | 8/2006 | Ray et al. |
| 2006/0224053 A1 | 10/2006 | Black et al. |
| 2006/0224152 A1 | 10/2006 | Behnke et al. |
| 2006/0291178 A1 | 12/2006 | Shih |
| 2007/0088413 A1 | 4/2007 | Weber et al. |
| 2007/0093801 A1 | 4/2007 | Behnke |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2008/0004619 A1 | 1/2008 | Malis et al. |
| 2008/0015563 A1 | 1/2008 | Hoey et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0132893 A1 | 6/2008 | D'Amelio et al. |
| 2008/0147056 A1 | 6/2008 | van der Weide et al. |
| 2008/0177199 A1 | 7/2008 | Podhajsky |
| 2008/0203997 A1 | 8/2008 | Foran et al. |
| 2008/0234574 A1 | 9/2008 | Hancock et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287943 A1 | 11/2008 | Weber et al. |
| 2008/0319350 A1 | 12/2008 | Wallace et al. |
| 2009/0018536 A1 | 1/2009 | Behnke |
| 2009/0030477 A1 | 1/2009 | Jarrard |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0234350 A1 | 9/2009 | Behnke et al. |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0248007 A1 | 10/2009 | Falkenstein et al. |
| 2009/0254077 A1 | 10/2009 | Craig |
| 2009/0259224 A1 | 10/2009 | Wham et al. |
| 2009/0292283 A1 | 11/2009 | Odom |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0082022 A1 | 4/2010 | Haley et al. |
| 2010/0082023 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0114090 A1 | 5/2010 | Hosier |
| 2010/0168572 A1 | 7/2010 | Sliwa et al. |
| 2010/0168730 A1 | 7/2010 | Hancock et al. |
| 2010/0168741 A1 | 7/2010 | Sanai et al. |
| 2010/0179533 A1 | 7/2010 | Podhajsky |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0268220 A1 | 10/2010 | Johnson et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert et al. |
| 2011/0071516 A1 | 3/2011 | Gregg |
| 2011/0071521 A1 | 3/2011 | Gilbert |
| 2011/0077631 A1 | 3/2011 | Keller |
| 2011/0077639 A1 | 3/2011 | Brannan et al. |
| 2011/0087213 A1 | 4/2011 | Messerly et al. |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0204903 A1 | 8/2011 | Gilbert |
| 2011/0208179 A1 | 8/2011 | Prakash et al. |
| 2011/0213354 A1 | 9/2011 | Smith |
| 2011/0213355 A1 | 9/2011 | Behnke, II |
| 2011/0301607 A1 | 12/2011 | Couture |
| 2011/0318948 A1 | 12/2011 | Plaven et al. |
| 2011/0319881 A1 | 12/2011 | Johnston |
| 2012/0004703 A1 | 1/2012 | Deborski et al. |
| 2012/0010610 A1 | 1/2012 | Keppel |
| 2012/0022521 A1 | 1/2012 | Odom et al. |
| 2012/0028373 A1 | 2/2012 | Belen et al. |
| 2012/0029515 A1 | 2/2012 | Couture |
| 2012/0089139 A1 | 4/2012 | Wham et al. |
| 2012/0101491 A1 | 4/2012 | Blaha |
| 2012/0116268 A1 | 5/2012 | Orszulak et al. |
| 2012/0130256 A1 | 5/2012 | Buysse et al. |
| 2012/0150170 A1 | 6/2012 | Buysse et al. |
| 2012/0172866 A1 | 7/2012 | Behnke, II |
| 2012/0179156 A1 | 7/2012 | Behnke, II |
| 2012/0220997 A1 | 8/2012 | Johnston |
| 2012/0239020 A1 | 9/2012 | Cunningham |
| 2012/0239025 A1 | 9/2012 | Smith |
| 2012/0239026 A1 | 9/2012 | Orszulak et al. |
| 2012/0265194 A1 | 10/2012 | Podhajsky |
| 2012/0265195 A1 | 10/2012 | Gilbert |
| 2012/0303017 A1 | 11/2012 | Brannan et al. |
| 2012/0310241 A1 | 12/2012 | Orszulak |
| 2012/0316555 A1 | 12/2012 | Orszulak et al. |
| 2012/0316556 A1 | 12/2012 | Podhajsky |
| 2013/0006235 A1 | 1/2013 | Podhajsky et al. |
| 2013/0023867 A1 | 1/2013 | Collins |
| 2013/0023869 A1 | 1/2013 | Orszulak |
| 2013/0023870 A1 | 1/2013 | Collins |

(56) References Cited

U.S. PATENT DOCUMENTS

| | | | |
|---|---|---|---|
| 2013/0023871 A1 | 1/2013 | Collins | |
| 2013/0035679 A1 | 2/2013 | Orszulak | |
| 2013/0041364 A2 | 2/2013 | Orszulak | |
| 2013/0041367 A1 | 2/2013 | Wham et al. | |
| 2013/0053840 A1 | 2/2013 | Krapohl et al. | |
| 2013/0066311 A1 | 3/2013 | Smith et al. | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079763 A1 | 3/2013 | Heckel et al. | |
| 2013/0158541 A1 | 6/2013 | Orszulak | |
| 2013/0178848 A1 | 7/2013 | Gilbert et al. | |
| 2013/0184698 A1 | 7/2013 | Behnke, II et al. | |
| 2013/0184699 A1 | 7/2013 | Behnke, II et al. | |
| 2013/0190750 A1 | 7/2013 | Behnke, II et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0324991 A1* | 12/2013 | Clem | A61B 17/320068 606/33 |
| 2013/0345696 A1 | 12/2013 | Behnke, II et al. | |
| 2014/0002056 A1 | 1/2014 | Moul et al. | |
| 2014/0015535 A1 | 1/2014 | Lopez | |
| 2014/0025064 A1 | 1/2014 | Collins et al. | |
| 2014/0163431 A1 | 6/2014 | Orszulak et al. | |
| 2015/0282822 A1* | 10/2015 | Trees | A61B 18/1445 606/41 |

FOREIGN PATENT DOCUMENTS

| | | | |
|---|---|---|---|
| DE | 1099658 B | 2/1961 | |
| DE | 1139927 B | 11/1962 | |
| DE | 1149832 B | 6/1963 | |
| DE | 1439302 A1 | 1/1969 | |
| DE | 2439587 A1 | 2/1975 | |
| DE | 2455174 A1 | 5/1975 | |
| DE | 2407559 A1 | 8/1975 | |
| DE | 2602517 A1 | 7/1976 | |
| DE | 2504280 A1 | 8/1976 | |
| DE | 2540968 A1 | 3/1977 | |
| DE | 2820908 A1 | 11/1978 | |
| DE | 2803275 A1 | 8/1979 | |
| DE | 2823291 A1 | 11/1979 | |
| DE | 2946728 A1 | 5/1981 | |
| DE | 3143421 A1 | 5/1982 | |
| DE | 3045996 A1 | 7/1982 | |
| DE | 3120102 A1 | 12/1982 | |
| DE | 3510586 A1 | 10/1986 | |
| DE | 3604823 A1 | 8/1987 | |
| DE | 3904558 A1 | 8/1990 | |
| DE | 3942998 A1 | 7/1991 | |
| DE | 4206433 A1 | 9/1993 | |
| DE | 4339049 A1 | 5/1995 | |
| DE | 19506363 A1 | 8/1996 | |
| DE | 19717411 A1 | 11/1998 | |
| DE | 19848540 A1 | 5/2000 | |
| DE | 102008058737 A1 | 4/2010 | |
| EP | 0246350 A1 | 11/1987 | |
| EP | 0267403 A2 | 5/1988 | |
| EP | 0296777 A2 | 12/1988 | |
| EP | 0309942 A2 | 4/1989 | |
| EP | 0310431 A2 | 4/1989 | |
| EP | 0325456 A2 | 7/1989 | |
| EP | 0336742 A2 | 10/1989 | |
| EP | 0390937 A1 | 10/1990 | |
| EP | 0503200 A2 | 9/1992 | |
| EP | 0556705 A1 | 8/1993 | |
| EP | 0569130 A1 | 11/1993 | |
| EP | 0608609 A2 | 8/1994 | |
| EP | 0617925 A1 | 10/1994 | |
| EP | 0694291 A1 | 1/1996 | |
| EP | 0836868 A2 | 4/1998 | |
| EP | 0870473 A2 | 10/1998 | |
| EP | 0878169 A1 | 11/1998 | |
| EP | 0880220 A2 | 11/1998 | |
| EP | 0882955 A1 | 12/1998 | |
| EP | 0640317 B1 | 9/1999 | |
| EP | 1051948 A2 | 11/2000 | |
| EP | 1053720 A1 | 11/2000 | |
| EP | 1146827 A1 | 10/2001 | |
| EP | 1151725 A1 | 11/2001 | |
| EP | 1157667 A2 | 11/2001 | |
| EP | 1263181 A1 | 12/2002 | |
| EP | 1278007 | 1/2003 | |
| EP | 1293171 A2 | 3/2003 | |
| EP | 1366724 A1 | 12/2003 | |
| EP | 1472984 A1 | 11/2004 | |
| EP | 1495712 A1 | 1/2005 | |
| EP | 1500378 A1 | 1/2005 | |
| EP | 1535581 A2 | 6/2005 | |
| EP | 1594392 A2 | 11/2005 | |
| EP | 1609430 A1 | 12/2005 | |
| EP | 1645235 A1 | 4/2006 | |
| EP | 1681026 A2 | 7/2006 | |
| EP | 1707143 | 10/2006 | |
| EP | 1707144 A1 | 10/2006 | |
| EP | 1744354 A2 | 1/2007 | |
| EP | 1776929 A1 | 4/2007 | |
| EP | 1810628 A1 | 7/2007 | |
| EP | 1810630 A1 | 7/2007 | |
| EP | 1810631 A2 | 7/2007 | |
| EP | 1810632 A1 | 7/2007 | |
| EP | 1810633 A2 | 7/2007 | |
| EP | 1810634 A1 | 7/2007 | |
| EP | 1849425 A1 | 10/2007 | |
| EP | 1854423 A2 | 11/2007 | |
| EP | 1862137 A1 | 12/2007 | |
| EP | 1902681 A1 | 3/2008 | |
| EP | 1994904 | 11/2008 | |
| EP | 2025297 A2 | 2/2009 | |
| EP | 2042116 A1 | 4/2009 | |
| EP | 2100566 A1 | 9/2009 | |
| EP | 2111812 A2 | 10/2009 | |
| EP | 2156800 A1 | 2/2010 | |
| EP | 2253286 A1 | 11/2010 | |
| EP | 2301463 A1 | 3/2011 | |
| EP | 2345454 A1 | 7/2011 | |
| FR | 1275415 A | 11/1961 | |
| FR | 1347865 A | 1/1964 | |
| FR | 2313708 A1 | 12/1976 | |
| FR | 2364461 A1 | 4/1978 | |
| FR | 2502935 A1 | 10/1982 | |
| FR | 2517953 A1 | 6/1983 | |
| FR | 2573301 A1 | 5/1986 | |
| GB | 607850 A | 9/1948 | |
| GB | 702510 A | 1/1954 | |
| GB | 855459 A | 11/1960 | |
| GB | 902775 A | 8/1962 | |
| GB | 1290304 A | 9/1972 | |
| GB | 2154881 A | 9/1985 | |
| GB | 2164473 A | 3/1986 | |
| GB | 2214430 A | 9/1989 | |
| GB | 2331247 A | 5/1999 | |
| GB | 2358934 A | 8/2001 | |
| GB | 2434872 A | 8/2007 | |
| JP | 63005876 | 1/1988 | |
| JP | 2002065690 A | 3/2002 | |
| JP | 2005185657 A | 7/2005 | |
| SU | 166452 | 11/1964 | |
| SU | 727201 A2 | 4/1980 | |
| WO | 9206642 | 4/1992 | |
| WO | 9207622 A1 | 5/1992 | |
| WO | 9320747 A1 | 10/1993 | |
| WO | 9324066 A1 | 12/1993 | |

(56)  References Cited

FOREIGN PATENT DOCUMENTS

| WO | 9410922 | A1 | 5/1994 |
|---|---|---|---|
| WO | 9424949 | A1 | 11/1994 |
| WO | 9428809 | A1 | 12/1994 |
| WO | 9509577 | A1 | 4/1995 |
| WO | 9518575 | A1 | 7/1995 |
| WO | 9519148 | A1 | 7/1995 |
| WO | 95/25472 | A1 | 9/1995 |
| WO | 9525471 | A2 | 9/1995 |
| WO | 9602180 | A2 | 2/1996 |
| WO | 9604860 | A1 | 2/1996 |
| WO | 9608794 | A1 | 3/1996 |
| WO | 9618349 | A2 | 6/1996 |
| WO | 9629946 | A1 | 10/1996 |
| WO | 96/39088 | A1 | 12/1996 |
| WO | 9639085 | A1 | 12/1996 |
| WO | 9639086 | A1 | 12/1996 |
| WO | 9639914 | A1 | 12/1996 |
| WO | 9706739 | A2 | 2/1997 |
| WO | 9706740 | A2 | 2/1997 |
| WO | 9706855 | A2 | 2/1997 |
| WO | 9710763 | A1 | 3/1997 |
| WO | 9711648 | A2 | 4/1997 |
| WO | 9717029 | A1 | 5/1997 |
| WO | 97/43971 | A2 | 11/1997 |
| WO | 9807378 | A1 | 2/1998 |
| WO | 9818395 | A1 | 5/1998 |
| WO | 9827880 | | 7/1998 |
| WO | 9912607 | A1 | 3/1999 |
| WO | 9956647 | A1 | 11/1999 |
| WO | 00/48672 | A1 | 8/2000 |
| WO | 0054683 | A1 | 9/2000 |
| WO | 0101847 | | 1/2001 |
| WO | 0200129 | | 1/2002 |
| WO | 0211634 | | 2/2002 |
| WO | 0232333 | | 4/2002 |
| WO | 0232335 | | 4/2002 |
| WO | 0245589 | A2 | 6/2002 |
| WO | 0247565 | | 6/2002 |
| WO | 02053048 | A1 | 7/2002 |
| WO | 02088128 | A1 | 11/2002 |
| WO | 03047446 | A1 | 6/2003 |
| WO | 03090635 | A1 | 11/2003 |
| WO | 03092520 | A1 | 11/2003 |
| WO | 03090630 | A3 | 4/2004 |
| WO | 2004028385 | A1 | 4/2004 |
| WO | 2004043240 | A2 | 5/2004 |
| WO | 2004047659 | A2 | 6/2004 |
| WO | 2004052182 | A2 | 6/2004 |
| WO | 2004073488 | | 9/2004 |
| WO | 2004098385 | A2 | 11/2004 |
| WO | 2004103156 | | 12/2004 |
| WO | 2005046496 | A1 | 5/2005 |
| WO | 2005048809 | | 6/2005 |
| WO | 2005050151 | | 6/2005 |
| WO | 2005060365 | A2 | 7/2005 |
| WO | 2005060849 | A1 | 7/2005 |
| WO | 2005115235 | A1 | 12/2005 |
| WO | 2005117735 | A1 | 12/2005 |
| WO | 2006050888 | A1 | 5/2006 |
| WO | 2006105121 | A2 | 10/2006 |
| WO | 2007055491 | A1 | 5/2007 |
| WO | 2007067522 | A2 | 6/2007 |
| WO | 2007076924 | A2 | 7/2007 |
| WO | 2007105963 | A1 | 9/2007 |
| WO | 2008002517 | A1 | 1/2008 |
| WO | 2008003058 | A2 | 1/2008 |
| WO | 2008011575 | A1 | 1/2008 |
| WO | 2008043999 | A2 | 4/2008 |
| WO | 2008044000 | A1 | 4/2008 |
| WO | 2008044013 | A2 | 4/2008 |
| WO | 2008053532 | A1 | 5/2008 |
| WO | 2008070562 | A1 | 6/2008 |
| WO | 2008071914 | A2 | 6/2008 |
| WO | 2008101356 | A1 | 8/2008 |
| WO | 2008110756 | A2 | 9/2008 |
| WO | 2010129348 | A1 | 11/2010 |

OTHER PUBLICATIONS

U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
4 U.S. Appl. No. 14/320,804 dated Jul. 1, 2014, inventor: Gilbert.
U.S. Appl. No. 13/971,553, filed Aug. 20, 2013, Behnke.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique For Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 no.2;(Mar. 2005); pp. 160-164.

(56)          References Cited

OTHER PUBLICATIONS

Chicharo et al. "A Sliding Goertzel Algorith" Aug. 1996, pp. 283-297, Signal Processing, Elsevier Science Publishers B.V. Amsterdam, NL vol. 52 no. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on esion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

U.S. Appl. No. 10/406,690 dated Apr. 3, 2003 inventor: Behnke.

U.S. Appl. No. 10/573,713 dated Mar. 28, 2006 inventor: Wham.

U.S. Appl. No. 10/761,524 dated Jan. 21, 2004 inventor: Wham.

U.S. Appl. No. 11/242,458 dated Oct. 3, 2005 inventor: Becker.

U.S. Appl. No. 14/096,341 dated Dec. 4, 2013 inventor: Johnson.

U.S. Appl. No. 14/098,859 dated Dec. 6, 2013 inventor: Johnson.

U.S. Appl. No. 14/100,113 dated Dec. 9, 2013 inventor: Gilbert.

U.S. Appl. No. 14/147,294 dated Jan. 3, 2014 inventor: Gilbert.

U.S. Appl. No. 14/147,312 dated Jan. 3, 2014 inventor: Gilbert.

U.S. Appl. No. 14/168,296 dated Jan. 30, 2014, inventor: Mattmiller.

U.S. Appl. No. 14/174,551 dated Feb. 6, 2014 inventor: Johnson.

U.S. Appl. No. 14/174,607 dated Feb. 6, 2014 inventor: Friedrichs.

U.S. Appl. No. 14/179,724 dated Feb. 13, 2014 inventor: Johnson.

U.S. Appl. No. 14/180,965 dated Feb. 14, 2014 inventor: Larson.

U.S. Appl. No. 14/181,114 dated Feb. 14, 2014 inventor: Larson.

U.S. Appl. No. 14/182,797 dated Feb. 18, 2014 inventor: Wham.

U.S. Appl. No. 14/190,830 dated Feb. 26, 2014 inventor: Johnson.

U.S. Appl. No. 14/190,895 dated Feb. 26, 2014 inventor: Johnson.

U.S. Appl. No. 14/255,051 dated Apr. 17, 2014 inventor: Coulson.

U.S. Appl. No. 14/262,219 dated Apr. 25, 2014, inventor: Gilbert.

U.S. Appl. No. 14/267,066 dated May 1, 2014, inventor: Friedrichs.

U.S. Appl. No. 14/268,187 dated May 2, 2014, inventor: Kerr.

U.S. Appl. No. 14/283,604 dated May 21, 2014, inventor: Behnke.

U.S. Appl. No. 14/297,771 dated Jun. 6, 2014, inventor: Wham.

* cited by examiner

MOTION SENSING ELECTROSURGICAL DEVICES

CROSS-REFERENCE TO RELATED APPLICATION

The present application claims the benefit of and priority to U.S. Provisional Application No. 63/209,090, filed on Jun. 10, 2021. The entire disclosure of the foregoing application is incorporated by reference herein.

BACKGROUND

Technical Field

The present disclosure relates to systems and methods for controlling an electrosurgical generator. In particular, the present disclosure relates to controlling an energy (e.g., electrosurgical or ultrasonic) generator using motion or position sensing electrosurgical devices.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Existing electrosurgical devices are relatively unsophisticated, with no integrated sensors. Thus, the burden is on the surgeon to adjust settings on the electrosurgical generator depending on the clinical scenario. Thus, there is a need for electrosurgical devices having sensors that would allow the generator to automatically adjusts settings.

SUMMARY

The present disclosure provides for incorporating position and/or motion sensors into various energy delivery device such as electrosurgical and ultrasonic instruments and for controlling energy generators powering the same. The sensors may be used in monopolar instrument to detect whether the surgeon is spot coagulating or cutting and adjust the electrosurgical output accordingly. Similarly, the sensors could be used in bipolar instruments to detect a touch and hold coagulation, grasping and pulling (i.e., dissecting) and adjusting electrosurgical or ultrasonic output accordingly.

Furthermore, the sensor data could be combined with electrical data to train a pattern recognition machine learning algorithm to detect surgeon intent (e.g. sealing, coagulating, cutting) and adjust the generator output accordingly.

According to one aspect of the disclosure, an electrosurgical system is disclosed. The electrosurgical system may include an electrosurgical generator configured to generate electrosurgical energy; and an electrosurgical instrument coupled to the electrosurgical generator. The electrosurgical instrument may include a motion and/or sensor, where the electrosurgical generator is configured to control the electrosurgical energy based on a sensor signal from the sensor.

Implementations of the above embodiment may include one or more of the following features. According to one aspect of the above embodiment, the electrosurgical generator may be configured operate in an automatic energy mode during which the electro surgical generator may be configured to output an interrogatory energy. The electrosurgical generator may be configured to determine tissue contact with the electrosurgical instrument based on impedance in response to the interrogatory energy. The electrosurgical generator may be further configured to output the electrosurgical energy based on determination of the tissue contact. The electrosurgical generator may be configured to deactivate the automatic energy mode based on an absence of the sensor signal from the sensor. The electrosurgical instrument may be one of a monopolar instrument, a bipolar forceps, or a bipolar tweezers. The electrosurgical instrument may be a bipolar forceps having a pair of opposing jaw members configured to grasp tissue. The electrosurgical generator may be configured to operate in a first electrosurgical mode and a second electrosurgical mode. The first electrosurgical mode may be configured to seal the tissue and the second electrosurgical mode may be configured to cut the tissue. The electrosurgical generator may be configured to switch between the first electrosurgical mode and the second electrosurgical mode based on the sensor signal from the sensor. The sensor may be configured to detect a cutting motion by the electrosurgical instrument.

According to another aspect of the disclosure, a method for controlling an electrosurgical generator is disclosed. The method may include generating electrosurgical energy at an electrosurgical generator; outputting a sensor signal from a motion and/or position sensor configured to detect motion of an electrosurgical instrument coupled to the electrosurgical generator; and controlling the electrosurgical energy based on the sensor signal.

Implementations of the above embodiment may include one or more of the following features. According to one aspect of the above embodiment, the method may include setting the electrosurgical generator to operate in an automatic energy mode during which the electrosurgical generator may be configured to output an interrogatory energy. The method may also include determining tissue contact with the electrosurgical instrument based on impedance in response to the interrogatory energy. The method may further include outputting the electrosurgical energy based on determination of the tissue contact. The method may further include deactivating the automatic energy mode based on an absence of the sensor signal from the sensor. The method may include grasping tissue between a pair of opposing jaw members; operating in a first electrosurgical mode and a second electrosurgical mode; and switching to a second electrosurgical mode based on the sensor signal from the sensor. The first electrosurgical mode may be configured to seal the tissue and the second electrosurgical mode may be configured to cut the tissue. The method may include detecting a cutting motion of the electrosurgical instrument based on the sensor signal from the sensor. The method may include deactivating a footswitch configured to activate the electrosurgical instrument based on an absence of the sensor signal from the sensor.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
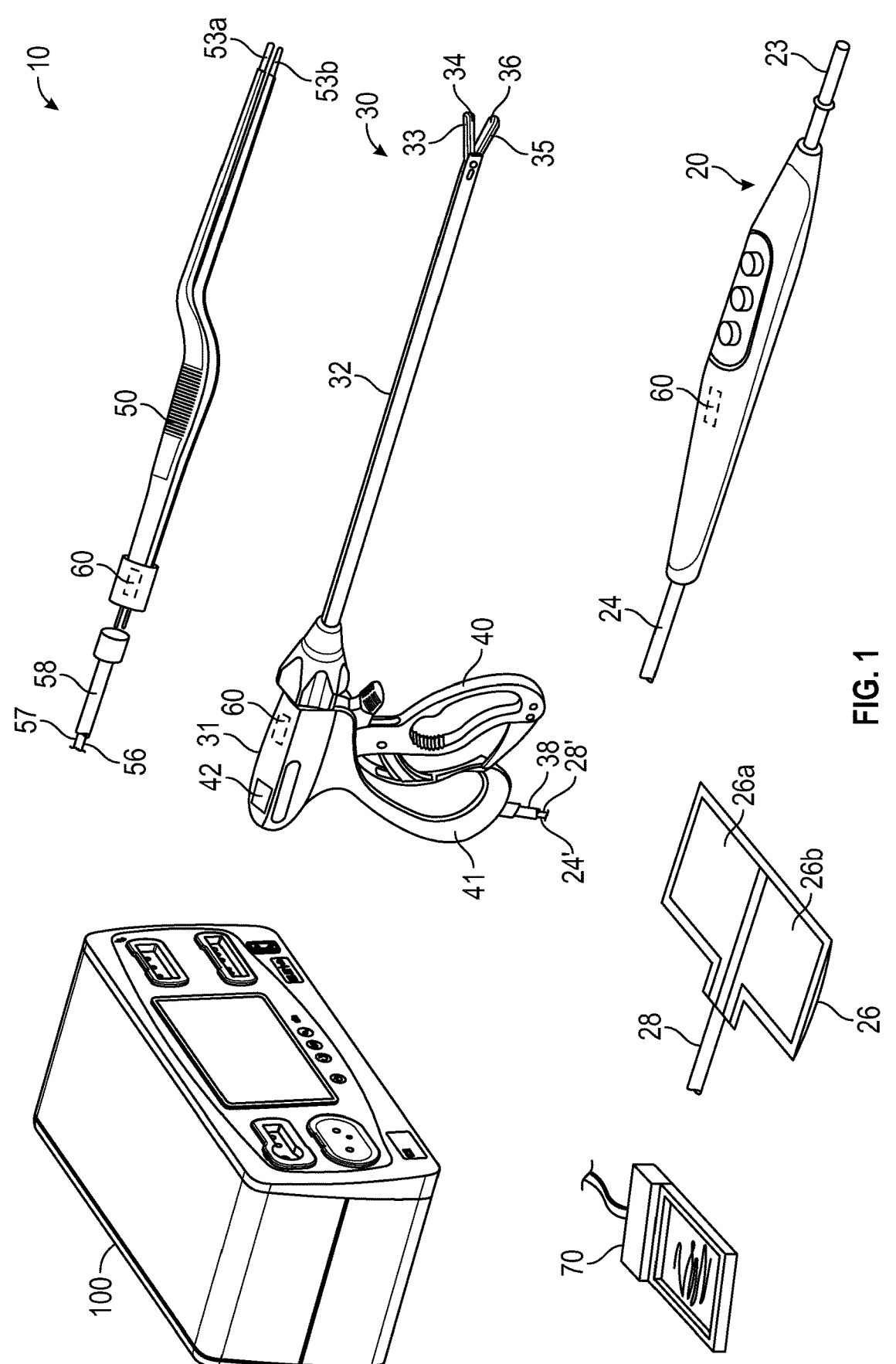
FIG. 1 is a perspective view of an electrosurgical system according to an embodiment of the present disclosure.

Embodiments of the presently disclosed system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Referring to FIG. 1 an electrosurgical system 10 is shown which includes one or more monopolar electrosurgical instruments 20 having an active electrode 23 (e.g., electrosurgical cutting probe, ablation electrode(s), etc.) for treating tissue of a patient. The system 10 may include a plurality of return electrode pads 26 that, in use, are disposed on a patient to minimize the chances of tissue damage by maximizing the overall contact area with the patient. Electrosurgical alternating RF current is supplied to the instrument 20 by a generator 100 via supply line 24. The alternating RF current is returned to the generator 100 through the return electrode pad 26 via a return line 28. In addition, generator 100 and the return electrode pads 26 may be configured for monitoring tissue-to-patient contact to ensure that sufficient contact exists therebetween. In particular, the return electrode pad 26 includes a pair of foil electrodes 26a and 26b, which are used to monitor tissue-to-patient contact by detecting a difference in electrical properties of the foil electrodes 26a and 26b.

Figure 3:
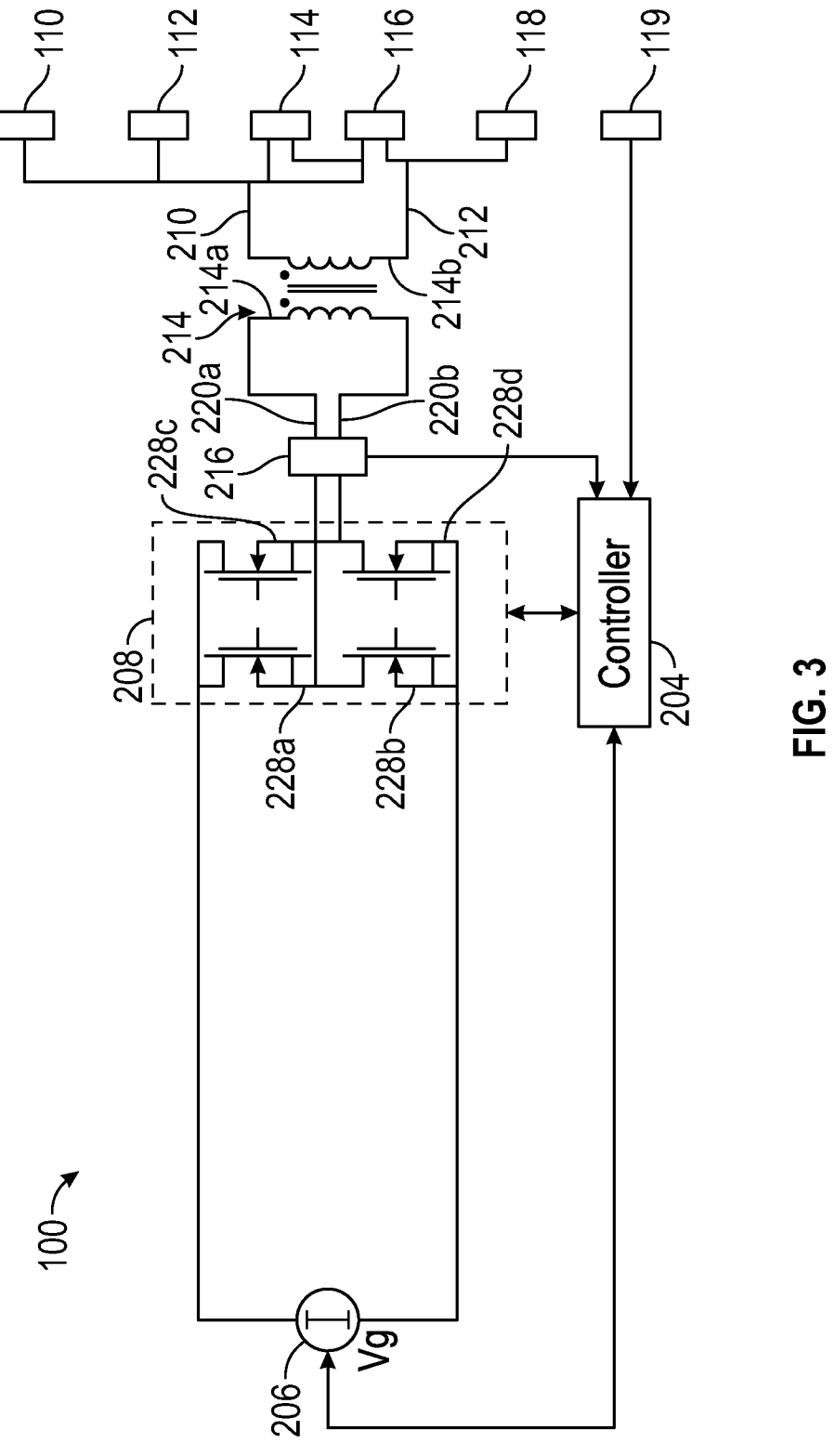
FIG. 3 is a schematic diagram of the electrosurgical generator of FIG. 1 according to an embodiment of the present disclosure.

The electrosurgical system 10 also includes one or more bipolar instruments, shown as electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 100 through cable 38 that includes the supply and return lines 24', 28', which may be coupled to the active and return terminals 210 and 212, respectively (FIG. 3). The electrosurgical forceps 30 is coupled to the generator 100 at a port having connections to the active and return terminals 210 and 212 (e.g., pins) via a plug disposed at the end of the cable 38, wherein the plug includes contacts from the supply and return lines 24', 28' as described in more detail below. The forceps 30 also includes a button 42 configured to signal to the generator 100 to output electrosurgical energy through the electrodes 34 and 36.

The forceps 30 also includes a lever 40 movable relative to a handle 41. The handle 41 is formed as part of the housing 31 and the lever 40 may be pivotably coupled within the housing 31. The lever 40 actuates, i.e., opens and closes, the jaw members 33 and 35, via one or more mechanical linkages. U.S. Pat. No. 8,784,418, titled "Endoscopic surgical forceps", provides additional disclosure of a bipolar electrosurgical forceps, the entire disclosure of which is incorporated by reference here. The lever 40 is movable from an open position (i.e., furthest distance from the handle 41) to a closed position (i.e., closest distance from the handle 41). The movement of the jaw members 33 and 35 corresponds to the movement of the lever 40. Thus, the jaw members are movable from an open position (i.e., furthest distance between the jaw members 33 and 35) to a closed position (i.e., closest between the jaw members 33 and 35, clamping tissue).

The electrosurgical system 10 also includes one or more bipolar electrosurgical instruments, which are shown as tweezers 50 having a pair of electrodes 53a and 53b, respectively, for treating tissue of a patient. The instrument 50 are coupled to a generator 100 via cable 58 having supply and return lines 56 and 57, respectively.

In addition, the electrosurgical system 10 also include a footswitch 70, which may be a pedal. The footswitch 70 may be paired to activate any one of the instrument 20, the forceps 30, or the tweezers 50 and may provide an alternative activation mechanism in addition to the user inputs on the generator 100 or any hand switches present on instruments. The footswitch 70 may include a plurality of buttons and/or switches configured to provide multiple user inputs.

Figure 2:
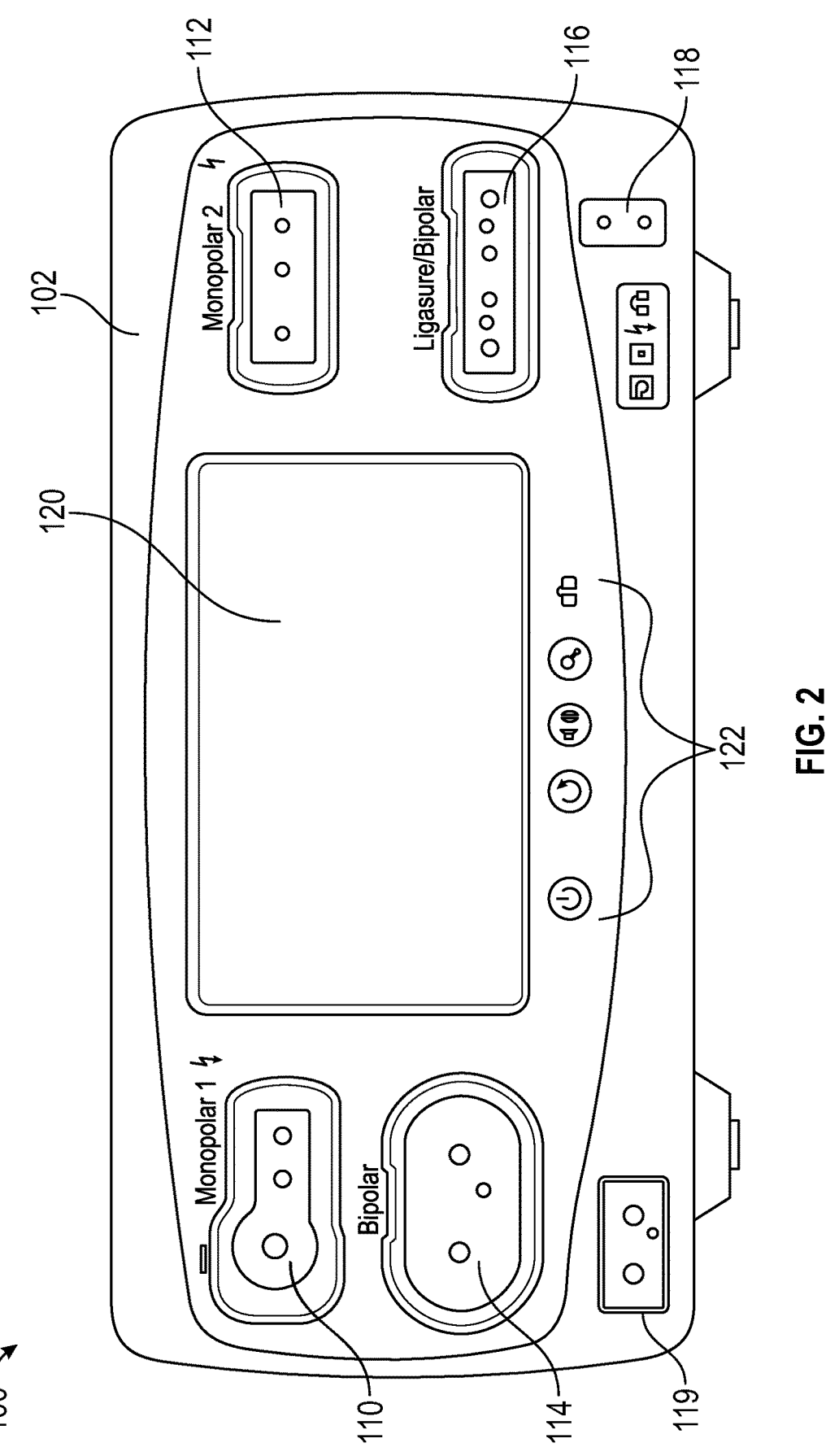
FIG. 2 is a front view of an electrosurgical generator of FIG. 1 according to an embodiment of the present disclosure.

With reference to FIG. 2, a front face 102 of the generator 100 is shown. The generator 100 may include a plurality of ports 110, 112, 114, 116 to accommodate various types of electrosurgical instruments and a port 118 for coupling to a return electrode pad and a port 119 configured to couple to the footswitch 70. The ports 110 and 112 are configured to couple to the monopolar electrosurgical instruments (e.g., first electrosurgical instrument 12). The ports 114 and 116 are configured to couple to bipolar electrosurgical instruments (e.g., second electrosurgical instrument 14). The generator 100 includes a display 120 for providing the user with variety of output information (e.g., intensity settings, treatment complete indicators, etc.). The display 120 is a touchscreen configured to display a menu corresponding to each of the ports 110, 112, 114, 116 and the instrument coupled. The user also adjusts inputs by touching corresponding menu options. The generator 100 also includes suitable input controls 122 (e.g., buttons, activators, switches, touch screen, etc.) for controlling the generator 100.

The generator 100 is configured to operate in a variety of modes and is configured to output monopolar and/or bipolar waveforms corresponding to the selected mode. Each of the modes may be activated by the button 42 disposed on the forceps 30. Each of the modes operates based on a preprogrammed power curve that limits how much power is output by the generator 100 at varying impedance ranges of the load (e.g., tissue). Each of the power curves includes power, voltage and current control ranges that are defined by the user-selected intensity setting and the measured minimum impedance of the load.

The generator 100 may operate in the following monopolar modes, which include, but are not limited to, cut, blend, division with hemostasis, fulgurate and spray. The generator 100 may operate in the following bipolar modes, including bipolar cutting, bipolar coagulation, automatic bipolar which operates in response to sensing tissue contact, and various algorithm-controlled vessel sealing modes. The generator 100 may be configured to deliver energy required to power an ultrasonic transducer. Thereby enabling control and modulation of ultrasonic surgical instruments.

Each of the RF waveforms may be either monopolar or bipolar RF waveforms, each of which may be continuous or discontinuous and may have a carrier frequency from about 200 kHz to about 500 kHz. As used herein, continuous waveforms are waveforms that have a 100% duty cycle. In embodiments, continuous waveforms are used to impart a cutting effect on tissue. Conversely, discontinuous waveforms are waveforms that have a non-continuous duty cycle, e.g., below 100%. In embodiments, discontinuous waveforms are used to provide coagulation effects to tissue.

With reference to FIG. 3, the generator 100 includes a controller 204, a power supply 206, and a RF inverter 208. The power supply 206 may be high voltage, DC power supplies connected to a common AC source (e.g., line voltage) and provide high voltage, DC power to their respective RF inverter 208, which then convert DC power into a RF waveform through active terminal 210 and return terminal 212 corresponding to the selected mode. The active terminal 210 and the return terminal 212 are coupled to the RF inverter 208 through an isolation transformer 214. The isolation transformer 214 includes a primary winding 214a coupled to the RF inverter 208 and a secondary winding 214b coupled to the active and return terminals 210 and 212.

Electrosurgical energy for energizing the monopolar electrosurgical instrument 20 is delivered through the ports 110 and 112, each of which is coupled to the active terminal 210. RF energy is returned through the return electrode pad coupled to the port 118, which in turn, is coupled to the return terminal 212. The secondary winding 214b of the isolation transformer 214 is coupled to the active and return terminals 210 and 212. RF energy for energizing a bipolar electrosurgical instrument is delivered through the ports 114 and 116, each of which is coupled to the active terminal 210 and the return terminal 212. The generator 100 may include a plurality of steering relays or other switching devices configured to couple the active terminal 210 and the return terminals 212 to various ports 110, 112, 114, 116, 118 based on the combination of the monopolar and bipolar electrosurgical instruments 20 and 30 being used.

The RF inverter 208 is configured to operate in a plurality of modes, during which the generator 100 outputs corresponding waveforms having specific duty cycles, peak voltages, crest factors, etc. It is envisioned that in other embodiments, the generator 100 may be based on other types of suitable power supply topologies. RF inverter 208 may be a resonant RF amplifier or non-resonant RF amplifier, as shown. A non-resonant RF amplifier, as used herein, denotes an amplifier lacking any tuning components, i.e., conductors, capacitors, etc., disposed between the RF inverter and the load, e.g., tissue.

The controller 204 may include a processor (not shown) operably connected to a memory (not shown). The controller 204 is operably connected to the power supply 206 and/or RF inverter 208 allowing the processor to control the output of the RF inverter 208 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to the controller 204. The controller 204 then controls the power supply 206 and/or RF inverter 208, which adjust the DC and/or RF waveform, respectively.

The generator 100 according to the present disclosure may also include a plurality of sensors 216, each of which monitors output of the RF inverter 208 of the generator 100. The sensor 216 may be any suitable voltage, current, power, and impedance sensors. The sensors 216 are coupled to leads 220a and 220b of the RF inverter 208. The leads 220a and 220b couple the RF inverter 208 to the primary winding 214a of the transformer 214. Thus, the sensors 216 are configured to sense voltage, current, and other electrical properties of energy supplied to the active terminal 210 and the return terminal 212.

In further embodiments, the sensor 216 may be coupled to the power supply 206 and may be configured to sense properties of DC current supplied to the RF inverter 208. The controller 204 also receives input (e.g., activation) signals from the display 120, the input controls 122 of the generator 100 and/or the instruments 20 and 30. The controller 204 adjusts power outputted by the generator 100 and/or performs other control functions thereon in response to the input signals.

The RF inverter 208 includes a plurality of switching elements 228a-228d, which are arranged in an H-bridge topology. In embodiments, RF inverter 208 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicon carbide, or any other suitable wide bandgap materials.

The controller 204 is in communication with the RF inverter 208, and in particular, with the switching elements 228a-228d. Controller 204 is configured to output control signals, which may be pulse-width modulated ("PWM") signals, to switching elements 228a-228d. In particular, controller 204 is configured to modulate a control signal supplied to switching elements 228a-228d of the RF inverter 208. The control signal provides PWM signals that operate the RF inverter 208 at a selected carrier frequency. Additionally, controller 204 is configured to calculate power characteristics of output of the RF inverter 208 of the generator 100, and control the output of the generator 100 based at least in part on the measured power characteristics including, but not limited to, voltage, current, and power at the output of RF inverter 208.

Each of the instruments 20, 30, 50 includes one or more motion and/or position sensors 60, which may be an accelerometer, a gyroscope, or any other suitable sensor configured to measure movement and/or tilt of the instruments 20, 30, 50. The sensors 60 enable sensing of tissue and/or instrument motion and adjust settings of the electrosurgical generator 100. The sensors 60 may be coupled to the generator 100 using any suitable wired or a wireless interface.

Figure 4:
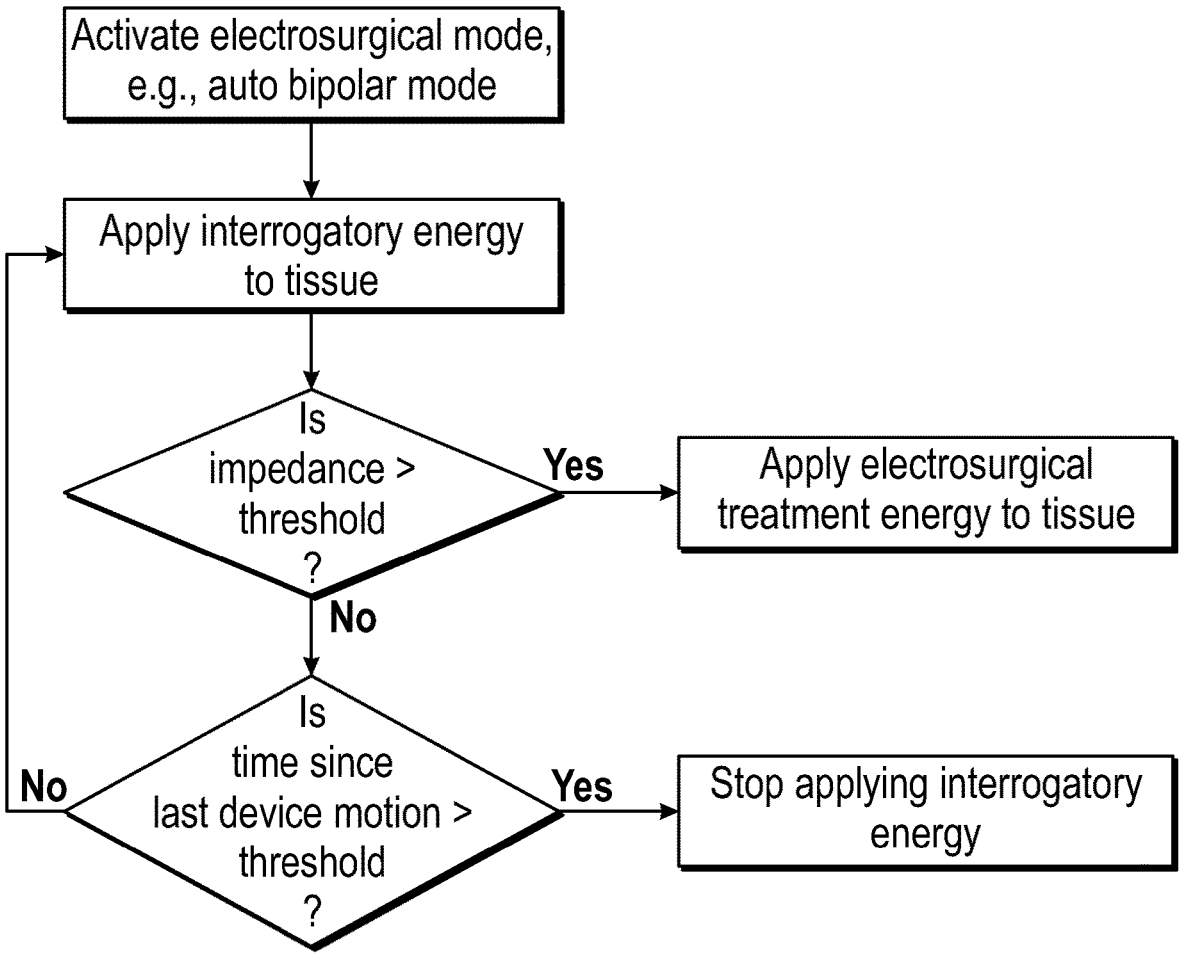
FIG. 4 is a flow chart of a method for controlling the electrosurgical generator of FIG. 1 according to one embodiment of the present disclosure.

FIG. 4 shows a flow chart for adjusting settings and/or output of the electrosurgical generator 100 based on feedback from the sensor 60 embedded in the bipolar instruments, such as the forceps 30 and the tweezers 50, or other instruments that operate in tissue contact-sensing modes, such as automatic bipolar. As described above, the generator 100 may be operated in an automatic bipolar mode. The user selects and activates the mode through the generator 100. Once enabled, the generator 100 outputs interrogatory energy to determine if there is tissue contact, i.e., if tissue is grasped by the forceps 30 or the tweezers 50. In embodiments, interrogatory energy may be a low power pulse, about 3 W having a duration of about 100 μsec which repeats about every 25 msec. The interrogatory energy is used to measure impedance of the instrument to determine if tissue is present since any grasped tissue would result in increased impedance. Once tissue contact is confirmed, the generator 100 outputs treatment energy, which may be any suitable electrosurgical waveform suitable for sealing and/or coagulating tissue.

The generator 100 also verifies if the bipolar instrument (i.e., the forceps 30 and the tweezers 50) has been left stationary for a predetermined time period. Thus, if the instrument has been left stationary for too long, the generator 100 exits the automatic bipolar mode, to prevent inadvertent activation. In embodiments, the time period may be from about 5 seconds to about 60 seconds. The generator 100 may run a timer that is reset every time the sensor 60 outputs a signal indicative of movement of bipolar instrument. Thus, if the generator 100 does not receive the signal from the sensor 60 within the prescribed time period, the generator 100 exits the electrosurgical mode. The time period may be settable by the user based on user preferences. Furthermore, the electrosurgical mode may be reenabled in response to detection of the motion.

Figure 5:
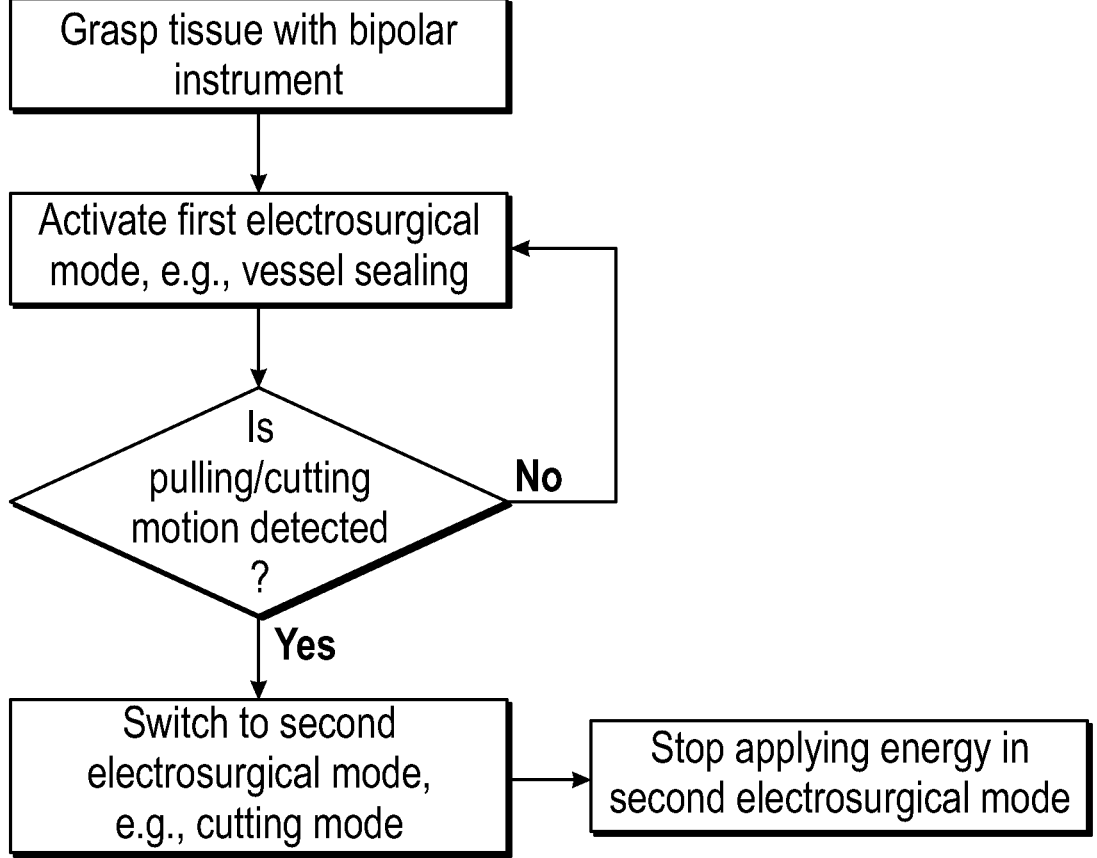
FIG. 5 is a flow chart of a method for controlling the electrosurgical generator of FIG. 1 according to one embodiment of the present disclosure.

FIG. 5 shows a flow chart for switching between different electrosurgical modes based on feedback from the sensor 60. Initially, tissue is grasped by a bipolar instrument, i.e., the forceps 30 or the tweezers 50. The user then activates energy in a first electrosurgical mode by pressing the button 42 or the footswitch 70. Once the first electrosurgical mode is activated, the energy is delivered until the user disables output or the generator 100 determines that treatment is completed, e.g., based on measured impedance. The first electrosurgical mode may be a continuous electrosurgical waveform suitable for sealing tissue. During energy delivery in the first electrosurgical mode, the generator 100 continuously monitors feedback from the sensor 60. The sensor 60 is configured to sense acceleration and/or velocity of the bipolar instrument. This allows the sensor 60 to detect grasping and/or pulling motion that the user performs during cutting of the tissue grasped by the bipolar instrument. Once the sensor 60 detects a cutting motion, the generator 100 switches from the first electrosurgical mode to a second electrosurgical cutting mode, which may be a pulsatile electrosurgical waveform suitable for cutting or separating tissue. The generator 100 stops the second electrosurgical mode automatically, i.e., based on measured impedance dropping below a threshold, or manually by the user pressing the button 42 or the footswitch 70.

The sensor 60 may also be used to adjust energy output of the selected electrosurgical mode. During cutting mode, the monopolar electrosurgical instrument 20 is activated and the active electrode 23 is dragged across tissue, which results in tissue dissection. The sensor 60 may be used to measure the speed of the monopolar electrosurgical instrument 20 and the generator 100 may adjust the duty cycle and/or power of the cutting electrosurgical waveform based on the speed at which the electro surgical instrument 20 is being moved. Thus, if the surgeon is dissecting faster, i.e., the monopolar electrosurgical instrument 20 is moved faster, a higher duty cycle waveform could be applied to speed up the dissection. If the surgeon is dissecting slower, the generator 100 may adjust a lower duty cycle waveform could be applied to increase hemostasis.

During coagulation mode, the monopolar electrosurgical instrument 20 is used to coagulate tissue and the active electrode 23 is repeatedly dragged across the tissue until sufficient coagulation is achieved. The sensor 60 may be used to detect repetitive motion in the same direction or bidirectional motion. This may be used to enhance spot coagulation such that once the generator 100 detects the repetitive motion of spot coagulation based on the feedback from the sensor 60, the generator 100 adjusts the duty cycle and/or power to optimize the coagulation waveform for spot coagulation.

Figure 6:
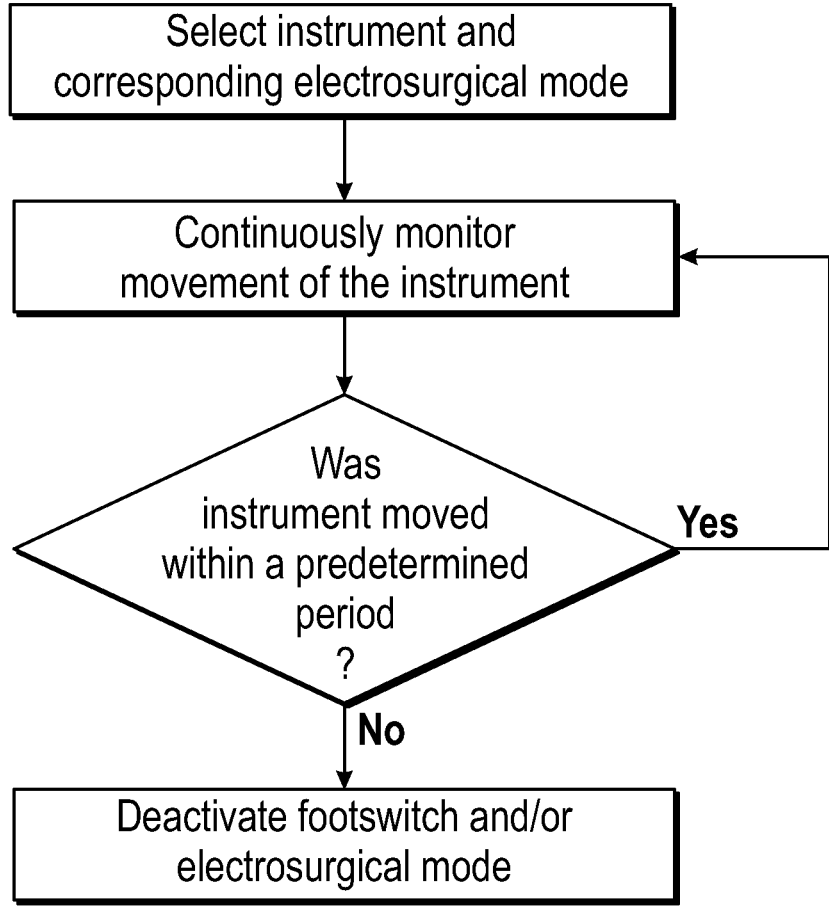
FIG. 6 is a flow chart of a method for controlling the electrosurgical generator of FIG. 1 according to one embodiment of the present disclosure.

The sensor 60 may also be used to disable the footswitch 70 based on detection that the instrument (i.e., the instrument 20, the forceps 30, and the tweezers 50) is no longer in use. As noted above, the footswitch 70 may be used to control any of the instruments coupled to the generator 100. The footswitch 70 may be used to activate and deactivate output of the generator 100 to the instrument. With reference to FIG. 6, a flow chart for activating/deactivating the footswitch 70 initially includes selecting the instrument and a corresponding electrosurgical mode. Once selected, the sensor 60 continuously detects movement of the instrument. The generator 100 is configured to deactivate the footswitch 70, such that the user does not inadvertently activate the instrument after a certain period of time has elapsed without any movement of the instrument. The period may be from about 5 seconds to about 30 seconds.

Feedback from the sensor 60 may also be used to adjust energy settings of the generator 100. Furthermore, the motion data may be stored in the generator 100 for subsequent retrieval. The motion data may be used to develop and train machine learning or other artificial intelligence algorithms to further enhance automatic energy setting adjustments. In addition, video or image data from cameras or endoscopes may be combined with motion data to optimize energy delivery and energy adjustment algorithms.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical system comprising:
an electrosurgical generator configured to generate electrosurgical energy; and
an electrosurgical instrument coupled to the electrosurgical generator, the electrosurgical instrument including a motion sensor configured to detect a speed at which the electrosurgical instrument is being moved, wherein, when the electrosurgical instrument is in contact with tissue, the electrosurgical generator is configured to control delivery of the electrosurgical energy to the electrosurgical instrument by adjusting a duty cycle of a radio-frequency cutting waveform based on the detected speed, including increasing the duty cycle for higher detected speeds and decreasing the duty cycle for lower detected speeds.

2. The electrosurgical system according to claim 1, wherein the electrosurgical instrument is selected from the group consisting of a monopolar instrument, a bipolar forceps, and a bipolar tweezers.

3. The electrosurgical system according to claim 1, wherein the electrosurgical instrument is a bipolar forceps having a pair of opposing jaw members configured to grasp tissue.

4. The electrosurgical system according to claim 3, wherein the electrosurgical generator is further configured to operate in a first electrosurgical mode and a second electrosurgical mode.

5. The electrosurgical system according to claim 4, wherein the first electrosurgical mode is further configured to seal the tissue and the second electrosurgical mode is configured to cut the tissue.

6. The electrosurgical system according to claim 5, wherein the electrosurgical generator is further configured to switch between the first electrosurgical mode and the second electrosurgical mode based on the sensor signal from the sensor.

7. The electrosurgical system according to claim 6, wherein the sensor is configured to detect a cutting motion by the electrosurgical instrument.

8. A method for controlling an electrosurgical generator, the method comprising:
generating electrosurgical energy at an electrosurgical generator;
grasping tissue between opposing jaw members of a bipolar forceps coupled to the electrosurgical generator;
outputting a sensor signal from a motion sensor of the bipolar forceps indicative of motion of the bipolar forceps;
while the tissue is grasped, detecting, based on the sensor signal, a cutting motion of the bipolar forceps; and
in response to detecting the cutting motion, controlling the electrosurgical energy by switching the electrosurgical generator from a first electrosurgical mode configured to seal tissue to a second electrosurgical mode configured to cut tissue.

9. The method according to claim 8, wherein the motion sensor includes at least one of an accelerometer or a gyroscope.

10. The method according to claim 8, wherein detecting the cutting motion of the bipolar forceps includes detecting at least one of an acceleration or a velocity of the bipolar forceps based on the sensor signal.

11. The method according to claim 8, wherein the first electrosurgical mode comprises delivering a continuous electrosurgical waveform suitable for sealing the tissue and the second electrosurgical mode comprises delivering a pulsatile electrosurgical waveform suitable for cutting the tissue.

12. The method according to claim 8, further comprising stopping delivery of the second electrosurgical mode automatically when an impedance measured between the opposing jaw members falls below a threshold.

13. The method according to claim 8, wherein detecting the cutting motion of the bipolar forceps includes detecting a grasping and pulling motion of the bipolar forceps while the tissue is grasped between the opposing jaw members.

* * * * *